United States Patent [19]

Cavazza et al.

[11] Patent Number: 5,045,306
[45] Date of Patent: Sep. 3, 1991

[54] N-ALKYLAMIDES OF D,L AND L(—)-CARNITINE HAVING ANTIBACTERIAL ACTIVITY, PROCESS FOR THEIR PREPARATION AND PHARMACEUTICAL AND COSMETIC COMPOSITIONS CONTAINING SAME

[75] Inventors: Paolo Cavazza; Giulio Fiorentini, both of Rome, Italy;

[73] Assignee: Avantgarde S.p.A., Pomezia, Italy

[21] Appl. No.: 267,185

[22] Filed: Nov. 4, 1988

[30] Foreign Application Priority Data

Dec. 2, 1987 [IT] Italy .................. 48663 A/87

[51] Int. Cl.$^5$ ................. A61K 7/22; A61K 7/15; A61K 31/16; C07C 237/50
[52] U.S. Cl. ..................... 424/54; 424/65; 424/73; 514/626; 564/197
[58] Field of Search ............ 564/197; 514/626; 424/54, 65, 76, 73

[56] References Cited

FOREIGN PATENT DOCUMENTS 0255807 10/1988 European Pat. Off. .
408435 1/1963 Japan .
62-298566 12/1987 Japan .
0054424 5/1943 Netherlands .

Primary Examiner—Richard L. Raymond
Assistant Examiner—P. O'Sullivan
Attorney, Agent, or Firm—Ladas & Parry

[57] ABSTRACT

N-alkylamide of DL and L(—)-carnitine having general formula (I)

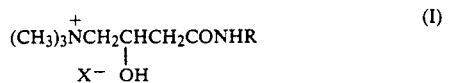

wherein:
$x^-$ is $OH^-$ or the anion of a pharmacologically acceptable acid (preferably $Cl^-$), and
R is a straight $C_{10}$–$C_{16}$ alkyl radical
are prepared via transamination by reacting DL or L(—)-carnitinamide halogenide with an amine of formula $NH_2R$ wherein R has the above-identified meaning in an acid environment (e.g. $H_3PO_4$) in the presence of a high-boiling solvent (e.g. ethylene glycol).

N-alkylamides (I) are endowed with potent antibacterial activity and are suitable for preparing pharmaceutical and cosmetic compositions.

6 Claims, No Drawings

N-ALKYLAMIDES OF D,L AND L(−)-CARNITINE HAVING ANTIBACTERIAL ACTIVITY, PROCESS FOR THEIR PREPARATION AND PHARMACEUTICAL AND COSMETIC COMPOSITIONS CONTAINING SAME

FIELD OF THE INVENTION

The present invention relates to novel N-alkylamides of D,L and L(−)-carnitine endowed with antibacterial activity, having general formula (I)

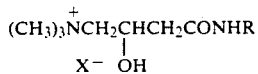

wherein
X− is OH− or the anion of a pharmacologically acceptable acid, and
R is a straight $C_{10}$–$C_{16}$ alkyl radical.
Preferably, X− is Cl−.

The present invention also relates to a process for producing N-alkylamides of formula (I) and pharmaceutical and cosmetic compositions comprising an amount of at least one of the N-alkylamides (I) suitable for promoting an effective antibacterial action.

BACKGROUND OF THE INVENTION

Some carnitine N-alkylamildes are known already.
In Japanese patent 408435 filed Oct. 31, 1960 in the name of Takeda Chemical Industries, Ltd. carnitinamides structurally analogous to those of formula (I) are disclosed, wherein, however, the radical R is lower alkyl (methyl and ethyl). This Japanese patent discloses that such amides "promote the intestinal peristalsis and are useful as medicaments for intestinal disorders". These amides are prepared by condensing at room temperature a reactive carnitine derivative (an acid halogenide, ester or anhydride) with methylamine or ethylamine.

DETAILED DESCRIPTION

The N-alkylamides of D,L and L(−)-carnitine according to the present invention are unlike the amides of Japanese Patent 408435 prepared via a process which comprises the following two characterizing steps:

(a) reacting an alkylamine of formula $NH_2R$ wherein R is a straight $C_{10}$–$C_{16}$ alkyl radical with a substantially equimolar amount of $H_3PO_4$, at 120°–140° C., for 2–4 hours, in an atmosphere of an inert gas, in the presence of a high-boiling solvent; and (b) adding to the reaction mixture a mixture of D,L or L(−)-carnitinamide chloride and alkylamine $NH_2R$, at a molar ratio of about 1:1.1, the molar amount of D,L or L(−)-carnitinamide chloride being about twice as much the molar amount of $H_3PO_4$ and keeping the resulting reaction mixture under stirring at about 110°–130° C. for about 34–38 hours in an atmosphere of inert gas.

After removal under vacuum of the high-boiling solvent, the residue comprising the N-alkylamide (I) is purified and the compound isolated according to known procedures.

The transamination of this process allows the direct conversion of the amide into the N-alkylamides (I) to be carried out. No intermediate steps are needed in order to convert the starting amide in one of those activated compounds (acid halogenides, esters or anhydrides) from which substituted amides are usually obtained (in this regard see the above mentioned Takeda patent). It is apparent that these intermediate steps would lower the yield remarkably and would increase the cost of the end product.

The following non-limiting example illustrates the preparation of one of the N-alkylamides (I) according to the process of this invention.

EXAMPLE

Preparation of D,L-N-dodecylcarnitinamide chloride

A mixture of dodecylamine (25 m moles), ethylene glycol (20.0 grams) and 85% H (25 m moles) was reacted in a 100-ml round bottom flask, sealed with a rubber stopper, under stirring, at 130° C. for 3 hours under nitrogen.

A mixture of D,L-carnitinamide chloride (50 m moles) and dodecylamine (55 m moles) was then added to the reaction mixture.

The resulting mixture was kept under stirring at 120° C. for 36 hours under nitrogen. When ammonia development ceased, the reaction mixture was cooled and ethylene glycol caused to evaporate at 80° C. under 0.5 mm Hg.

After the residue was dissolved in 80 ml of chloroform, the resulting solution was chromatographed on a silica (50 g) containing column. The product was first eluted with chloroform (100 ml) and with 100 ml of a 9:1 chloroform: isopropanol mixture; then, the product was eluted with 300 ml of a 1:1 chloroform:methanol mixture. The product was recovered by evaporation from the solvent. By further crystallization from 100 ml of tetrahydrofurane and then 100 ml of a 1:1 chloroform:tetrahydrofurane mixture (twice repeated) the title compound was obtained (Yield: 70%), $[\alpha]_D^{25} = 0$ Elementary analysis:
C=62.87%; H=11.50%; N=7.86%; Cl=10.25% O=7.52%.

Also the remaining N-alkylamides of D,L and L(−)-carnitine chloride encompassed in the general formula (I) were prepared by the same process. In the following table, the main chemico-physical characteristics of the compounds are listed.

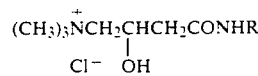

|  |  |  |  | Elementary Analysis | | IR spectra | |
|---|---|---|---|---|---|---|---|
| R | Abbreviated name | Molecular weight | $[\alpha]_D^{25}$ | Theoretical (%) | Found (%)(*) | Freq. $cm^{-1}$ | Assignments |
| $C_{10}H_{21}$ | L(−) CA-10 DL-CA-10 | 336.92 | −13.62° 0° | C = 60.60 H = 10.77 | C = 60.72 H = 10.54 | 950 1300 | —OH —CN— |

$(CH_3)_3\overset{+}{N}CH_2\underset{\underset{OH}{|}}{C}HCH_2CONHR$
$Cl^-$

| R | Abbreviated name | Molecular weight | $[\alpha]_D^{25}$ | Elementary Analysis Theoretical (%) | Found (%)(*) | IR spectra Freq. cm$^{-1}$ | Assignments |
|---|---|---|---|---|---|---|---|
| | | | | N = 8.31 | N = 8.85 | 1470 | CH$_2$ and OH |
| | | | | Cl = 10.52 | Cl = 10.00 | 1560 | —NH— |
| | | | | O = 9.50 | O = 8.89 | 1650 | $\overset{O}{\underset{}{\overset{\|}{C}}}$—NH— |
| C$_{11}$H$_{23}$ | L(−) CA-11 | 350.97 | −13.05° | C = 61.60 | C = 61.93 | 2940 | OH |
| | DL-CA-11 | | 0° | H = 10.91 | H = 11.29 | 3300 | OH |
| | | | | N = 7.98 | N = 8.05 | | The frequencies and the |
| | | | | Cl = 10.10 | Cl = 9.80 | | corresponding assignments |
| | | | | O = 9.12 | O = 8.84 | | can be regarded as identical |
| C$_{12}$H$_{25}$ | L(−) CA-12 | 364.97 | −12.60° | C = 62.53 | C = 62.87 | | for all the compounds |
| | DL-CA-12 | | 0° | H = 11.05 | H = 11.50 | | because the differences |
| | | | | N = 7.68 | N = 7.86 | | between them are not |
| | | | | Cl = 9.71 | Cl = 10.25 | | significant. |
| | | | | O = 8.77 | O = 7.52 | | |
| C$_{13}$H$_{27}$ | L(−) CA-13 | 379.03 | −12.23° | C = 63.34 | C = 63.65 | | |
| | DL-CA-13 | | 0° | H = 11.17 | H = 10.81 | | |
| | | | | N = 7.39 | N = 7.60 | | |
| | | | | Cl = 9.35 | Cl = 9.02 | | |
| | | | | O = 8.44 | O = 8.92 | | |
| C$_{14}$H$_{29}$ | L(−) CA-14 | 393.03 | −12.01° | C = 64.18 | C = 64.94 | | |
| | DL-CA-14 | | 0° | H = 11.28 | H = 12.00 | | |
| | | | | N = 7.13 | N = 7.19 | | |
| | | | | Cl = 9.02 | Cl = 9.87 | | |
| | | | | O = 6.14 | O = 6.00 | | |
| C$_{15}$H$_{31}$ | L(−) CA-15 | 407.08 | −11.62° | C = 64.91 | C = 64.99 | | |
| | DL-CA-15 | | 0° | H = 11.39 | H = 10.92 | | |
| | | | | N = 6.88 | N = 6.89 | | |
| | | | | Cl = 8.71 | Cl = 8.69 | | |
| | | | | O = 7.86 | O = 8.51 | | |
| C$_{16}$H$_{33}$ | L(−) CA-16 | 421.08 | −11.08 | C = 65.61 | C = 64.98 | | |
| | DL-CA-16 | | 0° | H = 11.49 | H = 11.87 | | |
| | | | | N = 6.65 | N = 6.64 | | |
| | | | | Cl = 8.42 | Cl = 8.97 | | |
| | | | | O = 7.60 | O = 7.54 | | |

(*) For both L(−) and DL form the "found" values are substantially identical.

TOXICOLOGICAL TESTS

1. Acute toxicity (1.1) Acute toxicity via the oral route in mice

It was evaluated in albino Swiss mice weighing 20-25 g which had been kept fasting 12 hours before administration.

The compounds dissolved in distilled water were administrated to the animals by gavage.

The animals were divided in groups of 6 animals each and treated with solutions of diminishing concentrations, each concentration being one half of the preceding concentration.

The mice were checked for 7 days following administration in order to verify their possible death or any behavioural alteration.

LD$_{50}$ was evaluated by the Carrol Weil method (Biometrics, Sept. 1952, pages 249-255, "Calculation of median-effective dose").

The results thus obtained are illustrated in table 1 and 1A.

TABLE 1

| | Acute Toxicity via the oral route in mice | | | |
|---|---|---|---|---|
| | DL-CA-10 | DL-CA-12 | DL-CA-14 | DL-CA-16 |
| LD$_{50}$ (mg/kg) | 791 | 1512 | 1125 | 1995 |

TABLE 1-continued

| | Acute Toxicity via the oral route in mice | | | |
|---|---|---|---|---|
| | DL-CA-10 | DL-CA-12 | DL-CA-14 | DL-CA-16 |
| Dose (mg/kg) | | | | |
| 4000 | — | 6/6 | 6/6 | 6/6 |
| 2000 | 6/6 | 5/6 | 6/6 | 3/6 |
| 1000 | 3/6 | 0/6 | 2/6 | 0/6 |
| 500 | 0/6 | 0/6 | 0/6 | 0/6 |
| 250 | 0/6 | — | — | — |

TABLE 1A

| | Acute Toxicity via the oral route in mice | | | |
|---|---|---|---|---|
| | L(-)-CA-10 | L(-)-CA-12 | L(-)-CA-14 | L(-)-CA-16 |
| LD$_{50}$ (mg/kg) | 890 | 1256 | 1125 | 1995 |
| Dose (mg/kg) | | | | |
| 4000 | — | 6/6 | 6/6 | 6/6 |
| 2000 | 6/6 | 6/6 | 6/6 | 2/6 |
| 1000 | 4/6 | 1/6 | 2/6 | 1/6 |
| 500 | 0/6 | 0/6 | 0/6 | 0/6 |
| 250 | 0/6 | — | — | — |

(1.2) Acute toxicity via the intravenous route in mice

It was evaluated in albino Swiss mice weighing 20-25 g.

The animals were injected the compounds dissolved in saline solution, in their caudal vein.

The animals were divided in groups of 6 animals each and treated with solutions of diminishing concentration, each concentration being one half of the preceding concentration. The mice were checked for 48 hours following administration.

$LD_{50}$ was evaluated by the Carrol Weil method.

The results are illustrated in table 2 and 2A.

TABLE 2

| Acute Toxicity via the intravenous route in mice | | | | |
| --- | --- | --- | --- | --- |
|  | DL-CA-10 | DL-CA-12 | DL-CA-14 | DL-CA-16 |
| $LD_{50}$ (mg/kg) | 28.28 | 25.2 | 48.72 | 63.33 |
| Dose (mg/kg) | | | | |
| 160 | — | — | 6/6 | 6/6 |
| 80 | 6/6 | 6/6 | 6/6 | 6/6 |
| 40 | 5/6 | 6/6 | 3/6 | 2/6 |
| 20 | 1/6 | 1/6 | 0/6 | 0/6 |
| 10 | 0/6 | 0/6 | — | — |

TABLE 2A

| Acute Toxicity via the intravenous route in mice | | | | |
| --- | --- | --- | --- | --- |
|  | L(-)-CA-10 | L(-)-CA-12 | L(-)-CA-14 | L(-)-CA-16 |
| $LD_{50}$ (mg/kg) | 28.28 | 25.2 | 63.33 | 56.42 |
| Dose (mg/kg) | | | | |
| 160 | — | — | 6/6 | 6/6 |
| 80 | 6/6 | 6/6 | 6/6 | 6/6 |
| 40 | 5/6 | 6/6 | 2/6 | 0/6 |
| 20 | 1/6 | 1/6 | 0/6 | 0/6 |
| 10 | 0/6 | 0/6 | — | — |

(1.3) Assessment of the irritating activity on the rabbit eye

The Federal Register test (vol. 38, 1973) modified as hereinbelow indicated was used.

Six New Zealand albino rabbits, weighing 1.5–2 kgs, were used for each test substance. Throughout the test the animals were caged so as to exclude possible extraneous materials that may produce eye irritation.

0.1 ml of a 1% solution of the test compounds was instilled with a dropper into the conjunctival sac of the rabbit right eye (the contralateral eye remained untreated and served as a control), whereupon the animals were caged again.

The treated eyes of all the animals were examined, in comparison with the control eye, 24, 48 and, if necessary, 72 hours following treatment.

The irritating activity was rated based on the scoring scale outlined in table 3.

The results are illustrated in table 4 and 4A.

TABLE 3

| Assessment of irritating activity on rabbit eyes | |
| --- | --- |
| Conjunctivae | |
| (a) Conjestion | |
| Vessels normal | 0 |
| Vessels slightly injected | 1 |
| Diffuse redness, vessels definetly injected not easily discernible | 2 |
| Diffuse, beefy red | 3 |
| (b) Chemosis | |
| No oedema | 0 |
| Slight oedema | 1 |
| Severe oedema with eversion of lids | 2 |
| Severe oedema with lids about half closed | 3 |
| Severe oedema with lids more than half closed | 4 |

TABLE 3-continued

| Assessment of irritating activity on rabbit eyes | |
| --- | --- |
| Cornea | |
| No alteration or opacity | 0 |
| Scattered or confluent areas of opacity; details of iris visible | 1 |
| Easily discernible translucent areas; details of iris slightly obscured | 2 |
| Nacreous area; no details of iris visible; contours of pupil barely discernible | 3 |
| Complete corneal opacity; iris not discernible | 4 |
| Iris | |
| Normal | 0 |
| Markedly deepened folds, more numerous than normal; congestion, swelling, moderate circumcorneal injection; iris still reacting to light | 1 |
| No reaction to light; haemorrhage; gross destruction | 2 |

TABLE 4

| Assessment of irritation activity on rabbit eyes | | | | |
| --- | --- | --- | --- | --- |
| RABBIT No. | DL-CA-10 irritation score | DL-CA-12 irritation score | DL-CA-14 irritation score | DL-CA-16 irritation score |
| 1 | 2 | 2 | 4 | 2 |
| 2 | 2 | 4 | 4 | 4 |
| 3 | 0 | 2 | 0 | 4 |
| 4 | 0 | 2 | 0 | 2 |
| 5 | 2 | 2 | 2 | 6 |
| 6 | 2 | 2 | 2 | 2 |
| Average score | 1.3 | 2.3 | 2.0 | 3.3 |

TABLE 4A

| Assessment of irritaiton activity on rabbit eyes | | | | |
| --- | --- | --- | --- | --- |
| RABBIT No. | L(-)-CA-10 irritation score | L(-)-CA-12 irritation score | L(-)-CA-14 irritation score | L(-)-CA-16 irritation score |
| 1 | 2 | 2 | 2 | 6 |
| 2 | 0 | 2 | 4 | 4 |
| 3 | 2 | 4 | 0 | 0 |
| 4 | 2 | 0 | 0 | 2 |
| 5 | 2 | 2 | 2 | 4 |
| 6 | 0 | 4 | 2 | 2 |
| Average score | 1.3 | 2.3 | 1.5 | 3 |

(1.4) Assessment of the cutaneous irritation activity in rabbits

Irritation to the skin was evaluated by the method illustrated in Federal Register (vol. 38, No. 187, page 27019, 1973) on albino rabbits weighing about 2 kgs.

Two days before the test was commenced, the back of the rabbits was clipped free of hair with an electric shearing machine, taking care not to bring about irritations and abrasions.

At test beginning, a zone of the skin was abraded by a sterile syringe needle.

Both on the intact and abraded skin an AL-test patch soaked in a 20% solution of the test compound was secured in place.

Similar patches (controls) soaked in the same volume of saline solution were secured in place on the intact and abraded skin.

The AL-test patches were secured in place to the animals by antiallergic adhesive plasters After 24 hours of exposures the patches were removed and the skin examined.

The reactions were evaluated at 24 and 72 hours on the basis of the table in Federal Register (see table 5).

The results thus obtained are illustrated in table 6 and 6A.

TABLE 5

Assessment of the cutaneous irritating activity
SKIN REACTIONS:

(1) ERYTHEMA
- No erythema — 0
- Slight barely perceptible erythema — 1
- Well-defined erythema — 2
- Moderate to severe erythema — 3
- Severe erythema (intense redness) to slight eschar formation — 4

(2) OEDEMA
- No oedema — 0
- Slight, barely perceptible oedema — 1
- Slight oedema (with well-defined edges) — 2
- Moderate oedema (raised approximately 1 mm) — 3
- Severe oedema (raised more than 1 mm and

TABLE 5-continued

Assessment of the cutaneous irritating activity
SKIN REACTIONS:

extending beyond the exposure area) — 4

The reaction value is the average of the values of six animals and is calculated by adding the values under 1) to the values under 2) for both intact and abraded skin. The resulting sum is divided by 24 and the result is termed "primary cutaneous irritation score".

The substance is regarded as:
- non-irritating if the score is 0
- mildly irritating if the score ranges between 0 and 2
- averagely irritating if the score ranges between 2 and 5
- severely irritating if the score ranges between 5 and 8

TABLE 6

Assessment of the cutaneous irritating activity

| | | DL-CA-10 (*) | | | | | DL-CA-12 (**) | | | | |
|---|---|---|---|---|---|---|---|---|---|---|---|
| | | Erythema value after | | Oedema value after | | | Erythema value after | | Oedema value after | | |
| Rabbit | Skin | 24 hours | 72 hours | 24 hours | 72 hours | Total | 24 hours | 72 hours | 24 hours | 72 hours | Total |
| 1 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| 2 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| 3 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| 4 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| 5 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| 6 | intact | 0 | 0 | 0 | 0 | 0 | 0 | 0 | 2 | 0 | 4 |
| | abraded | 0 | 0 | 0 | 0 | 0 | 0 | 0 | 2 | 0 | |
| irritation score | | | | 0 | | | | | 1 | | |

| | | DL-CA-14 (**) | | | | | DL-CA-16 (*) | | | | |
|---|---|---|---|---|---|---|---|---|---|---|---|
| | | Erythema value after | | Oedema value after | | | Erythema value after | | Oedema value after | | |
| Rabbit | Skin | 24 hours | 72 hours | 24 hours | 72 hours | Total | 24 hours | 72 hours | 24 hours | 72 hours | Total |
| 1 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| 2 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| 3 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| 4 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| 5 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| 6 | intact | 0 | 0 | 0 | 0 | 0 | 0 | 0 | 0 | 0 | 0 |
| | abraded | 0 | 0 | 0 | 0 | 0 | 0 | 0 | 0 | 0 | 0 |
| irritation score | | | | 0 | | | | | 0 | | |

(*) Exposure period: 4 hours
(**) Exposure period: 24 hours

TABLE 6A

Assessment of the cutaneous irritating activity

| | | L(-)-CA-10 (*) | | | | | L(-)-CA-12 (**) | | | | |
|---|---|---|---|---|---|---|---|---|---|---|---|
| | | Erythema value after | | Oedema value after | | | Erythema value after | | Oedema value after | | |
| Rabbit | Skin | 24 hours | 72 hours | 24 hours | 72 hours | Total | 24 hours | 72 hours | 24 hours | 72 hours | Total |

TABLE 6A-continued

Assessment of the cutaneous irritating activity

| Rabbit | Skin | | | | | | | | | | Total |
|---|---|---|---|---|---|---|---|---|---|---|---|
| 1 | intact | 0 | 0 | 0 | 0 | 0 | 0 | 0 | 2 | 0 | 4 |
|   | abraded | 0 | 0 | 0 | 0 | 0 | 0 | 0 | 2 | 0 | |
| 2 | intact | 0 | 0 | 0 | 0 | 0 | 0 | 0 | 2 | 0 | 4 |
|   | abraded | 0 | 0 | 0 | 0 | 0 | 0 | 0 | 2 | 0 | |
| 3 | intact | 0 | 0 | 0 | 0 | 0 | 0 | 0 | 2 | 0 | 4 |
|   | abraded | 0 | 0 | 0 | 0 | 0 | 0 | 0 | 2 | 0 | |
| 4 | intact | 0 | 0 | 0 | 0 | 0 | 0 | 0 | 2 | 0 | 4 |
|   | abraded | 0 | 0 | 0 | 0 | 0 | 0 | 0 | 2 | 0 | |
| 5 | intact | 0 | 0 | 0 | 0 | 0 | 0 | 0 | 2 | 0 | 4 |
|   | abraded | 0 | 0 | 0 | 0 | 0 | 0 | 0 | 2 | 0 | |
| 6 | intact | 0 | 0 | 0 | 0 | 0 | 0 | 0 | 2 | 0 | 4 |
|   | abraded | 0 | 0 | 0 | 0 | 0 | 0 | 0 | 1 | 0 | |
| irritation score | | 0 | | | | | | 1 | | | |

| | | L(-)-CA-14 (**) | | | | | L(-)-CA-16 (*) | | | | |
|---|---|---|---|---|---|---|---|---|---|---|---|
| | | Erythema value after | | Oedema value after | | | Erythema value after | | Oedema value after | | |
| Rabbit | Skin | 24 hours | 72 hours | 24 hours | 72 hours | Total | 24 hours | 72 hours | 24 hours | 72 hours | Total |
| 1 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| 2 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| 3 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| 4 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| 5 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| 6 | intact | 0 | 0 | 0 | 0 | 0 | 0 | 0 | 0 | 0 | 0 |
|   | abraded | 0 | 0 | 0 | 0 | 0 | 0 | 0 | 0 | 0 | 0 |
| irritation score | | 0 | | | | | 0 | | | | |

(*) Exposure period: 4 hours
(**) Exposure period: 24 hours

ANTIBACTERIAL ACTIVITY in vitro 1.1 Determination of antibacterial activity on Petri plates The test was carried out on sterile Petri plates (14 cm of diameter), by inoculating the strains listed at point A in suitable culture media by the Kirby-Bauer method.

A)
1 - Bacillus subtilis ATCC 6633 on Müller Hinton agar
2 - Escherichia coli ATCC 25922 on Müller Hinton agar
3 - Staphylococcus aureus ATCC 6538 on Müller Hinton agar
4 - Mucor mucedo ATCC 7941 on Sabouraud maltose agar
5 - Candida albicans ATCC 2091 on Sabouraud maltose agar The antibacterial activity of the compounds was evaluated by means of a well on the solidified medium. The results are shown in table 7 and 7A.

TABLE 7

| | | Antibacterial Activity (diameter in mm) | | | | |
|---|---|---|---|---|---|---|
| Concentration | (DL) Compound | E. coli | Staph. aureus | Bac. subtilis | Cand. albic. | Mucor mucedo (*) |
| 0.1% | C10 | 10.7 | 10.8 | 14.0 | 12.7 | + - |
| | C12 | 19.1 | 16.9 | 18.0 | 17.3 | - + |
| | C14 | 10.6 | 10.3 | 10.9 | 13.4 | + - |
| | C16 | 10.4 | 10.6 | 9.9 | 13.5 | - |
| 1% | C10 | 14.1 | 14.6 | 27.1 | 24.0 | + + |
| | C12 | 28.6 | 19.8 | 23.0 | 24.8 | + + + |
| | C14 | 12.7 | 13.0 | 12.4 | 16.8 | + - |
| | C16 | 11.0 | 12.4 | 11.0 | 14.7 | - |
| 10% | C12 | 30.6 | 21.8 | 27.0 | 25.0 | + + + |
| | C14 | 15.4 | 18.1 | 17.0 | 17.9 | + - |
| | C16 | 11.4 | 16.1 | 14.6 | 16.0 | + |
| | DL-carnitina-mide-chloride | — | — | — | — | — |

(*) + - = 10.0 to 12.0 mm in diameter
+ = 12.0 to 19.0 mm in diameter
+ + = 19.0 to 29.0 mm in diameter
+ + + = 29.0 to 35.0 mm in diameter

TABLE 7A

| | | Antibacterial Activity (diameter in mm) | | | | |
|---|---|---|---|---|---|---|
| Concentration | (DL) Compound | E. coli | Staph. aureus | Bac. subtilis | Cand. albic. | Mucor mucedo (*) |
| 0.1% | C10 | 10.8 | 11.5 | 13.0 | 12.3 | - - |
| | C12 | 20.7 | 15.6 | 19.0 | 18.2 | - + |
| | C14 | 10.6 | 11.4 | 10.1 | 13.8 | - - |

TABLE 7A-continued

| Con-centra-tion | (DL) Compound | Antibacterial Activity (diameter in mm) | | | | Mucor mucedo (*) |
|---|---|---|---|---|---|---|
| | | E. coli | Staph. aureus | Bac. subtilis | Cand. albic. | |
| | C16 | 10.9 | 10.6 | 9.6 | 12.0 | + |
| 1% | C10 | 14.8 | 15.3 | 24.1 | 21.0 | ++ |
| | C12 | 28.8 | 18.8 | 26.0 | 23.9 | +++ |
| | C14 | 11.0 | 14.1 | 12.9 | 16.1 | + |
| | C16 | 10.6 | 13.2 | 11.5 | 13.0 | + |
| 10% | C12 | 30.6 | 20.5 | 27.9 | 24.8 | +++ |
| | C14 | 16.3 | 19.6 | 18.1 | 19.3 | + |
| | C16 | 11.5 | 15.9 | 13.6 | 16.4 | + |
| | DL-carnitina-mide-chloride | — | — | — | — | — |

(*) +− = 10.0 to 12.0 mm in diameter
+ = 12.0 to 19.0 mm in diameter
++ = 19.0 to 29.0 mm in diameter
+++ = 29.0 to 35.0 mm in diameter in vitro 2.1 Determination of Minimum Inhibiting Concentration (MIC)

The test was carried out on sterile Petri dishes (10 cm of diameter) loaded with 10 ml of medium and anti-bacterial substance at given concentration, mixed at 9:1 ratio.

The medium used was
(1) Müller Hinton agar for bacteria, and
(2) Sabouraud Dextrose agar for fungi The solidified plates were then inoculated at the surface thereof with a multi-point inoculator equipped with 48 rods, each of which had been coated with a suspension of the tested microorganism. The suspensions were prepared with the Kirby-Bauer method (Bauer, Kirby, Sherris, Turck 1966, Am. J. Clin. Pathol. 45:49-496) modified according to D'Amato-Hochstein (D'Amato-Hochstein, 1982, J. Clin. Microb. 15 (2) 282-285).

The inoculated plates were incubated at 35° C. (culture medium (1)) and 25° C. (culture medium (2)) respectively.

Reading was carried out after 15-18 hours for bacteria and after 24-30 hours for fungi.

MIC values thus obtained are shown in table 8 and 8A.

TABLE 8

Minimum Inhibiting Concentration (mcg)
Method: Petri dishes with solid culture medium

| | | DL-CA-10 | DL-CA-12 | DL-CA-14 | DL-CA-16 |
|---|---|---|---|---|---|
| Staphylococcus aureus | 10547 | 62 | 15 | 15 | 15 |
| " | 8530 | 62 | 31 | 15 | 15 |
| " | 6538P | 31 | 62 | 250 | >500 |
| " | 80R | 62 | 15 | 15 | 15 |
| " | 58R | 62 | 62 | 31 | 31 |
| Enterococcus | 1 Renz. | 62 | 7 | <7 | <7 |
| " | 2 Renz. | 62 | 7 | <7 | <7 |
| Strept. faecalis lactis R | 8043 | 62 | <7 | <15 | <7 |
| " | 66/48 | 62 | 7 | <7 | <7 |
| Strept. faecium | UM | 31 | <7 | <7 | <7 |
| Sarcina lutea | 9341 | 250 | 62 | 62 | 15 |
| Bacillus subtilis | 6633 | 62 | 15 | 15 | 31 |
| Pseudomonas aeruginosa | 3E | >500 | 250 | >500 | >500 |
| " | 50F | >500 | 250 | >500 | >500 |
| " | 12F | >500 | 125 | >500 | >500 |
| Salmonella typhi | SK | 125 | 62 | 250 | >500 |
| Salmonella typhi | 6539 | 62 | 31 | 15 | 31 |
| Enterobacter cloacae | P99 β-Latt. | 250 | 31 | 125 | >500 |
| Shigella somnei | SK | 125 | 62 | 200 | >500 |
| Escherichia coli | 4 | 125 | 62 | 250 | >500 |
| " | 828 | 500 | 125 | >500 | >500 |
| " | 92F | 250 | 62 | 250 | >500 |
| " | 66/46 | 125 | 62 | >500 | >500 |
| " | R57B | 250 | 125 | >500 | 500 |
| Klebsiella pneumoniae | IB 1 (pat.) | 500 | 31 | 250 | 500 |
| Candida albicans | A 215 | 250 | 62 | 15 | 125 |
| " | i6 | 250 | 62 | 15 | 62 |
| " | ISS 562 | 250 | 62 | 15 | 62 |
| Candida tropicalis | ISS 5705 | 250 | <7 | 31 | 7 |
| Mucor mucedo | 7941 | 250 | 15 | 15 | 62 |
| Aspergillus niger | 9642 | 500 | 15 | 15 | 15 |

TABLE 8A

Minimum Inhibiting Concentration (mcg)
Method: Petri dishes with solid culture medium

| | | L(-)-CA-10 | L(-)-CA-12 | L(-)-CA-14 | L(-)-CA-16 |
|---|---|---|---|---|---|
| Staphylococcus aureus | 10547 | 31 | 15 | 15 | 15 |
| " | 8530 | 31 | 31 | 62 | 15 |
| " | 6538P | 62 | 62 | 250 | >500 |
| " | 80R | 62 | 15 | 15 | 15 |
| " | 58R | 62 | 15 | 15 | 15 |
| Enterococcus | 1 Renz. | 62 | 7 | 15 | <7 |
| " | 2 Renz. | 62 | 7 | <7 | <7 |
| Strept. faecalis lactis R | 8043 | 62 | <7 | <7 | 15 |
| " | 66/48 | 62 | 7 | <7 | <7 |
| Strept. faecium | UM | 31 | <7 | <7 | <7 |
| Sarcina lutea | 9341 | 125 | 62 | 62 | 31 |

TABLE 8A-continued

Minimum Inhibiting Concentration (mcg)
Method: Petri dishes with solid culture medium

|  |  | L(-)-CA-10 | L(-)-CA-12 | L(-)-CA-14 | L(-)-CA-16 |
|---|---|---|---|---|---|
| Bacillus subtilis | 6633 | 125 | 15 | 15 | 31 |
| Pseudomonas aeruginosa | 3E | >500 | 250 | >500 | >500 |
| " | 50F | >500 | 62 | >500 | >500 |
| " | 12F | >500 | 125 | >500 | >500 |
| Salmonella typhi | SK | 125 | 62 | 250 | 250 |
| Salmonella typhi | 6539 | 62 | 31 | 15 | 31 |
| Enterobacter cloacae | P99 β-Latt. | 125 | 62 | 125 | >500 |
| Shigella somnei | SK | 125 | 62 | 200 | >500 |
| Escherichia coli | 4 | 125 | 62 | 250 | >500 |
| " | 828 | 250 | 125 | >500 | >500 |
| " | 92F | 500 | 62 | 500 | >500 |
| " | 66/46 | 125 | 125 | >500 | >500 |
| " | R57B | 500 | 250 | >500 | >500 |
| Klebsiella pneumoniae | IB 1 (pat.) | 500 | 62 | 250 | >500 |
| Candida albicans | A 215 | 250 | 62 | 15 | 125 |
| " | i6 | 250 | 62 | 15 | 62 |
| " | ISS 562 | 250 | 31 | 31 | 31 |
| Candida tropicalis | ISS 5705 | 250 | <7 | 31 | 15 |
| Mucor mucedo | 7941 | 250 | 15 | 15 | 62 |
| Aspergillus niger | 9642 | 500 | 15 | 31 | 15 |

ANTIDANDRUFF ACTIVITY in vitro

3. DL and L(−) activity on Pityrosporum ovalis ATCC 12078

The test was carried out on sterile Petri plates having 10 cm of diameter filled with 10 ml of medium inoculated with the tested microorganism.

Sabouraud maltose agar + 1% Tween 80 was used as culture medium.

The Kirby-Bauer method modified according to D'Amato-Hochstein was used.

The plates after inoculation by means of wells on the agar-containing medium were incubated at 35° C. for 48 hours.

The diameter of the growth inhibition zone was 20.3 mm for the 1% DL solution and 20.5 mm for the 1% L(−) solution and 9.91 mm for the 0.1% DL solution and 10.2 for the 0.1% L(−) solution.

3.2 Minimum inhibiting concentration of DL and L(−) CA-12 on Pityrosporum ovalis ATCC 12078

The test was carried out following the method outlined at point 2.1, except that the medium was modified by the addition of 1% Tween 80. The resulting MIC was 50 mcg for both DL and L(−).

The compounds of the invention are suitable for being compounded into pharmaceutical, cosmetic and over-the-counter (OTC) compositions, such as mouthwashes, external disinfectants, deodorants, shaving creams and the like. It was found that, generally, the optimum concentration of N-alkylamides of formula (I) in the compositions is 0.1–0.3% by weight for a preservative action and 0.3–1% by weight for a disinfectant action.

Some compositions according to the invention are hereinbelow indicated.

| Alcoholic deodorant | |
|---|---|
| Ethanol | 42 g |
| Perfume | 0.1 g |
| DL or L(-) CA-12 | 0.1 g |
| Propylene glycol | 3 g |
| Softigen 767 | 0.5 g |
| Deionized water | balance to 100 g |
| Alcohol-free deodorant | |
| Ethanol | 3 g |

| -continued | |
|---|---|
| Solulan C 24 | 1 g |
| Perfume | 0.1 g |
| Propylene glycol | 3 g |
| DL or L(-) CA-12 | 0.1 g |
| Lanidrol (lanolin alcohol) | 0.5 g |
| Deionized water | balance to 100 g |
| Shaving cream | |
| Esso wax 5250 | 6 g |
| Marcol 52 | 6.5 g |
| Laurex CS | 10 g |
| Tween 60 | 3 g |
| Silicone oil AK 350 | 1 g |
| Butylhydroxyanisole | 0.05 g |
| Steinamid P256 | 1.7 g |
| DL or L(-) CA-12 | 0.15 g |
| EDTA (ethylenediaminetetraacetic acid) | 0.2 g |
| Propylene glycol | 3 g |
| Empigen BT | 5 g |
| Polimer JR 400 | 0.1 g |
| Perfume | 0.35 g |
| Deionized water | balance to 100 g |
| Liquid detergent | |
| Empilan 2574 | 1 g |
| Tween 20 | 2.4 g |
| Tween 80 | 1.5 g |
| Empigen BT | 40 g |
| Zetesol 250 | 7.6 g |
| Neo extrapon lemon | 0.1 g |
| Sigma antioxidant | 0.1 g |
| EDTA | 0.1 g |
| DL or L(-) CA-12 | 0.15 g |
| Solulan 16 | 0.6 g |
| Phosphoric acid | 0.12 g |
| Coconut oil diethanolamide | 3 g |
| Deionized water | balance to 100 g |
| Chewing gum | |
| Chlorofil | 0.0027 g |
| Sodium fluoride | 0.0152 g |
| DL or L(-) CA-12 | 0.667 g |
| Micronized sorbitol | 35.78 g |
| Micronized mannitol | 13.55 g |
| Gum base | 28.74 g |
| Aroma | 0.282 g |
| Menthol | 0.406 g |
| 70% sorbitol solution | 17.35 g |

What is claimed is:

1. N-alkylamides of DL and L(−)-carnitine having general formula (I)

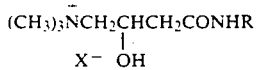 (I)

wherein:
- $X^-$ is $OH^-$) or the anion of a pharmacologically acceptable acid, and
- R is a straight $C_{10}-C_{16}$ alkyl radical.

2. N-alkylamides of DL and L(−)-carnitine according to claim 1, wherein $X^-$ is $Cl^-$.

3. A composition suitable for topical application having antibacterial activity which comprises an amount effective for exerting a disinfectant action of a first component comprising at least one of the N-alkylamides of DL and L(−)-carnitine of claim 1, and a second component comprising a carrier or diluent.

4. The composition of claim 3 comprising about 0.3–1.0% by weight of one of the N-alkylamides of DL and L(−)-carnitine of claim 1.

5. The composition of claim 3 wherein the second component is a carrier which is a pharmaceutically or cosmetically acceptable vehicle for the topical application of said composition.

6. The composition of claim 5 wherein the pharmaceutically or cosmetically acceptable vehicle makes said composition suitable for topical application as a mouthwash, external disinfectant, deodorant, face cream, body cream or shaving cream.

* * * * *